United States Patent [19]
Hirsch

[11] 3,989,462
[45] Nov. 2, 1976

[54] TEST COMPOSITION FOR DETECTING UROBILINOGEN
[75] Inventor: Wolfgang Hirsch, Luthe, Germany
[73] Assignee: Riedel-de Haen Aktiengesellschaft, Seelze, Hannover, Germany
[22] Filed: May 10, 1976
[21] Appl. No.: 684,798

[30] Foreign Application Priority Data
May 14, 1975 Germany............................ 2521402

[52] U.S. Cl. ......................... 23/253 TP; 23/230 B; 252/408
[51] Int. Cl.² ................. G01N 21/06; G01N 31/22; G01N 33/16
[58] Field of Search .................... 23/253 TP, 230 B; 252/408

[56] References Cited
UNITED STATES PATENTS

| | | |
|---|---|---|
| 3,446,599 | 5/1969 | Shand............................... 23/230 B |
| 3,630,680 | 12/1971 | Rittersdorf et al................ 23/230 B |
| 3,814,586 | 6/1974 | Fraser, Jr. et al................ 23/253 TP |
| 3,850,576 | 11/1974 | Rittersdorf et al................ 23/230 B |
| 3,853,466 | 12/1974 | Rittersdorf et al................ 23/230 B |

Primary Examiner—Robert M. Reese
Attorney, Agent, or Firm—Connolly and Hutz

[57] ABSTRACT

4-Fluoro-3-nitrobenzenediazonium salts in test compositions capable of specific and sensitive determination of urobilinogen without any interference of bilirubin in an aqueous solution or body fluid such as urine. The diazonium salts have incorporated special stabilizing anions. In addition to a 4-fluoro-3-nitrobenzene diazonium salt, the test compositions preferably include an acid constituent capable of producing an acid pH upon contacting the solution to be tested. The test device comprises a bibulous carrier member, such as paper impregnated with the test composition in dry form.

7 Claims, No Drawings

TEST COMPOSITION FOR DETECTING UROBILINOGEN

This invention relates to a test composition for detecting urobilinogen in liquids, especially in biological fluids and more especially in urine.

It is known to detect urobilinogen with the use of a solution of dimethylaminobenzaldehyde in hydrochloric acid. In the course of time this test, known as Ehrlich reaction, has gained considerable importance in medical diagnostics, although it is not very specific. Nowadays, the detection of urobilinogen in urine has become a standard method for the diagnosis of liver and gall-bladder diseases.

In the growing field of the application of agents for rapid diagnosis test papers have been developed permitting to detect urobilinogen on the basis of the Ehrlich reaction. These papers have, of course, the unspecificity of the Ehrlich test and, moreover, they have the disadvantage that the color reaction develops very slowly.

It is also known that urobilinogen reacts with diazotized amines. This so-called yellow diazo reaction is, however, not used in medical laboratories.

Recently, test papers for detecting urobilinogen in liquids using the diazo reaction have been described (cf. British Pat. No. 1,343,247, German Pat. No. 2,130,559 and German Offenlegungsschriften 2,229,611 and 2,364,844). As reagents there are used aromatically substituted or anellated, stable phenyl-, pyrrole- and pyrazole-diazonium salts (German Offenlegungsschrift No. 2,229,611, U.S. Pat. No. 3,850,676) or substituted benzidine derivatives (German Offenlegungsschrift No. 2,364,844, U.S. Pat. No. 3,814,586). In another patent (German Pat. No. 2,130,559, British Pat. No. 1,343,247) the use of stable benzene diazonium salts containing in ortho or para position at least one polyatomic electron donor group capable of mesomerism is described in which the sum of the Hammet sigma values of all substituents must not exceed a value of 0.4.

The test papers using the diazo reaction are generally less liable to perturbations than the papers on the basis of the Ehrlich reaction. But in many cases they show a reaction also with bilirubin, a bile pigment likewise occuring in the urine on the occasion of gall-bladder and liver diseases.

It has surprisingly been found that compounds of the formula I

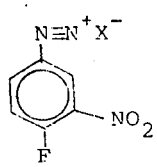

I in which $X^-$ represents a stabilizing anion are excellently suitable for the detection of urobilinogen. They represent sensitive and specific reagents for urobilinogen and do not react with bilirubin, although the sum of the Hammett sigma values of all substituents is 0.77.

The stabilizing anion of the compounds of formula I can be a chloride, a sulfate, a tetrafluoroborate, a hexafluoroantimonate, a hexafluoroantimony sulfonate, a trifluoromethyl sulfonate, an aryl sulfonate, or a carboxylic acid radical.

Diazonium salts of formula I are especially suitable, optionally in combination with one or several solid acids and/or a stabilizer and/or a wetting agent and/or an optical brightener, for use as an absorbent paper.

The compounds of the invention react with urobilinogen within a few seconds with the formation of red pigments. The color reaction is not disturbed by the natural constituents of urine, for example indican occuring in urine and urea. The diazonium compounds of the invention do not react either with bilirubin, so that it becomes possible to detect specifically uribilinogen if these two compounds are simultaneously present.

This fact is very surprising, the more so as in German Auslegeschrift No. 2,130,559, column 4, lines 26 to 29 it has been stated that the reaction with bilirubin can be suppressed by adding as indicator a diazonium salt having a relatively low electron affinity. As compared therewith, in the present case when both constituents are simultaneously present a high specificity is obtained with a diazonium compound of relatively high electron affinity.

The compounds of formula I are preferably used for the manufacture of test papers. For this purpose they are applied to an absorbent carrier together with an acid and optionally other additives such as stabilizers, wetting agents and brighteners.

For the manufacture an absorbent carrier, preferably paper or a non woven fabric of polyester fibers, is impregnated with a solution of the specified composition in a mixture consisting of an organic solvent miscible with water and water and then dried in circulating air at a temperature of from 0° to 80° C.

The diazonium compound of formula I, which is added to the impregnating solution in an amount of from 0.02 to 2 grams, preferably 0.1 to 0.5 gram per 100 ml of solution, can be prepared in accordance with the usual methods of diazo chemistry, or it is produced in the impregnating solution from the corresponding aromatic amine by a process known in diazo chemistry.

Suitable solid acids, which are added to the impregnating solution in an amount of from 1 to 30 grams, preferably 5 to 15 grams, per 100 ml of solution, are organic aromatic and aliphatic carboxylic acids or sulfonic acids, either separately or in admixture, also with inorganic acids. Stabilizers such as the disodium salt of naphthalene-1,5-disulfonic acid or sodium lauryl sulfate are well known in diazo chemistry. They can be added to the impregnating solution in an amount of from 1 to 10 grams, preferably 1 to 7 grams, per 100 ml of solution.

Wetting agents such as dodecylbenzene sulfonic acid or sodium lauryl sulfate can be added to the impregnating solution in an amount of from 0.1 to 5 grams, preferably 0.5 to 1 gram, per 100 ml of solution.

Optical brighteners, which are added to improve the readability, can be used in an amount of from 0.01 to 5 grams, preferably 0.1 to 2 grams, per 100 ml of impregnating solution. Suitable brighteners are stilbene derivatives as sold by Messrs. Bayer AG, Germany, under the name of Blankophor[(R)].

As solvent water can be used in admixture with an organic solvent mixcible with water, preferably a low molecular weight alcohol, for example methanol. The ratio of water to oganic solvent is not critical and is solely determined by the solubility of the components.

Suitable absorbent carriers are filter papers or non wovens made of polyamide or polyester or other acid-resistant plastic materials. It is immaterial of which absorbent material the carrier is made. It is also possible to use other materials capable of absorbing the impregnating solution. The individual components of the impregnating solution may, of course, also be applied to the carrier one after the other if the solubility or special circumstances necessitate such a proceeding.

Alternatively, the compounds of formula I can be used for the test in the form of a solution. For this purpose, a solution is prepared as indicated above. The solution to be examined is then suitably dropped into the said solution. In this case, the use of an optical brightener is not necessary. The urobilinogen content is determined either by comparison with a color chart or by means of a spectrophotometer.

To carry out the tests with the solutions described above the impregnated carrier is dipped for a short while into the liquid to be tested. After a few seconds the change in color becomes visible and may be compared with a color chart.

The following examples illustrate the invention.

Filter paper no. 2316 of Messrs. Schleicher & Schull, Germany, was impregnated with solutions having the following compositions, and dried at room temperature.

EXAMPLE 1

1 gram of 4-fluoro-3-nitrobenzene diazonium fluoroborate
10 ml of methanol
2 grams of sulfosalicylic acid
about 100 ml of water After having been dipped into urine containing urobilinogen the test paper showed a red color within 10 to 15 seconds.

EXAMPLE 2

0.1 gram of 4-fluoro-3-nitrobenzene diazonium salt
10 ml of methanol
10 grams of meta-phosphoric acid
3 grams of citric acid 1-hydrate
1 gram of dodecylbenzene sulfonic acid
about 100 ml of water The following diazonium salts were used: 4-fluoro-3-nitrobenzene diazonium tetrafluoroborate, trifluoromethyl sulfonate and hexafluoroantimony sulfonate.

All test papers of this example detected 0.5 mg of urobilinogen in 100 ml solution and showed a red color when dipped into urine containing urobilinogen.

EXAMPLE 3

0.1 gram of 4-fluoro-3-nitrobenzene diazonium tetrafluoroborate
10 ml of methanol
3 grams of citric acid 1-hydrate
10 grams of meta-phosphoric acid
1 gram of the disodium salt of naphthalene-1,5-disulfonic acid
1 gram of dodecylbenzenesulfonic acid
1 gram of brightener (Blankophor PSL$^{(R)}$; Bayer AG)
about 100 ml of water.

When a test paper according to this example was dipped into normal urine, the color changed from pink to red to dark red, depending on the urobilinogen content.

Similar colorations, having however a slightly more yellowish appearance due to the yellow color shade inherent to bilirubin, are obtained by adding to the urine samples prior to the test 10 mg each of bilirubin per 100 ml of solution. In the contrary, the test agent within a comparable period of time does not show any color reaction with urine free from urobilinogen, but containing bilirubin; only yellow colorations of various intensity degrees are observed due to the yellow color of bilirubin. Whilst after 5 minutes no reaction can be detected, a slightly green coloration shows after 10 – 15 minutes.

What is claimed is:

1. Test composition for detecting urobilinogen in liquids, preferably in biological fluids, especially in urine, comprising a diazonium salt of the formula I

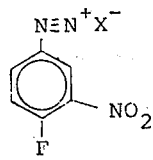

in which $X^-$ represents a stabilizing anion selected from the group consisting of a chloride, sulfate, tetrafluoroborate, hexafluoroantimonate, hexafluoroantimony sulfonate, trifluoromethyl sulfonate, aryl sulfonate, or carboxylic acid radical and at least one solid acid and optionally a wetting agent and one or several stabilizers.

2. Test composition as claimed in claim 1, which contains additionally a wetting agent.

3. Test composition as claimed in claim 1, which contains additionally at least one stabilizer.

4. Test combination as claimed in claim 1, which contains additionally an optical brightener.

5. Test composition as claimed in claim 1, supported on an absorbent carrier.

6. Test composition as claimed in claim 1, which contains additionally a wetting agent and at least one stabilizer.

7. Test composition as claimed in claim 6, wherein the diazonium salt is 4-fluoro-3-nitrobenzene diazonium tetrafluoroborate, the acid is a mixture of meta-phosphoric acid and citric acid, the wetting agent is dodecylbenzenesulfonic acid and the stabilizer is the disodium salt of naphthalene-1,5-disulfonic acid.

* * * * *